(12) United States Patent
John et al.

(10) Patent No.: US 9,020,585 B2
(45) Date of Patent: *Apr. 28, 2015

(54) ELECTRONIC IDENTITY CARD (75) Inventors: Erwin Roy John, Mamaroneck, NY (US); Leslie S. Prichep, Mamaroneck, NY (US)

(73) Assignee: New York University, New York, NY (US)

( * ) Notice: Subject to any disclaimer, the term of this patent is extended or adjusted under 35 U.S.C. 154(b) by 924 days.

This patent is subject to a terminal disclaimer.

(21) Appl. No.: 12/665,000

(22) PCT Filed: Jun. 17, 2008

(86) PCT No.: PCT/US2008/067221
§ 371 (c)(1),
(2), (4) Date: May 12, 2010

(87) PCT Pub. No.: WO2008/157544
PCT Pub. Date: Dec. 24, 2008

(65) Prior Publication Data
US 2011/0118618 A1 May 19, 2011

Related U.S. Application Data

(60) Provisional application No. 60/944,687, filed on Jun. 18, 2007.

(51) Int. Cl.
*A61B 5/04* (2006.01)
*A61B 5/117* (2006.01)
*A61B 5/0476* (2006.01)
*A61B 5/0484* (2006.01)
*A61B 5/00* (2006.01)

(52) U.S. Cl.
CPC ............... *A61B 5/117* (2013.01); *A61B 5/0476* (2013.01); *A61B 5/0484* (2013.01); *A61B 5/411* (2013.01)

(58) Field of Classification Search
USPC .................................................. 600/544, 545
See application file for complete search history.

(56) References Cited

U.S. PATENT DOCUMENTS

| 4,545,388 | A | * | 10/1985 | John | ............................ 600/544 |
| 4,846,190 | A | | 7/1989 | John | |
| 5,027,817 | A | | 7/1991 | John | |
| 6,016,444 | A | | 1/2000 | John | |
| 6,052,619 | A | | 4/2000 | John | |
| 6,067,467 | A | | 5/2000 | John | |

(Continued)

*Primary Examiner* — Etsub Berhanu
(74) *Attorney, Agent, or Firm* — Fay Kaplun & Marcin, LLP (57) ABSTRACT

A method comprises the steps of obtaining a baseline measurement corresponding to a representation of brain activity from a living body and storing the baseline measurements on a storage device configured to be wearable on the living body in combination with obtaining, at a time subsequent to the baseline measurement, a second measurement representing brain activity from the living body, reading the baseline measurement from the storage device and evaluating the living body based on a comparison of the second measurement to the baseline measurement. A system for analyzing electrical brain activity, the system comprises a component for reading, from a storage medium, data corresponding to a baseline measurement of brain activity of a living body and a component for determining data representing a current brain activity of the living body in combination with a component for evaluating the living body by comparing the baseline measurement data and the current brain activity data.

47 Claims, 3 Drawing Sheets

(56) References Cited

U.S. PATENT DOCUMENTS

| | | |
|---|---|---|
| 6,556,861 B1 | 4/2003 | Prichep |
| 6,575,902 B1 * | 6/2003 | Burton .......................... 600/300 |
| 7,089,927 B2 | 8/2006 | John et al. |
| 2002/0165436 A1 * | 11/2002 | Schluter et al. ............... 600/300 |
| 2003/0171689 A1 * | 9/2003 | Millan et al. .................. 600/544 |
| 2005/0070777 A1 * | 3/2005 | Cho et al. ...................... 600/365 |
| 2005/0197590 A1 * | 9/2005 | Osorio et al. ................. 600/544 |
| 2006/0074340 A1 * | 4/2006 | Murata ......................... 600/558 |
| 2006/0089541 A1 * | 4/2006 | Braun et al. ................... 600/300 |
| 2006/0094972 A1 * | 5/2006 | Drew ............................. 600/523 |
| 2006/0217816 A1 * | 9/2006 | Pesaran et al. ................... 623/25 |
| 2006/0270916 A1 * | 11/2006 | Skwarek et al. .............. 600/300 |
| 2007/0027367 A1 * | 2/2007 | Oliver et al. .................. 600/300 |
| 2007/0032737 A1 * | 2/2007 | Causevic et al. .............. 600/544 |
| 2007/0156030 A1 * | 7/2007 | Richardson .................. 600/300 |
| 2007/0249955 A1 * | 10/2007 | Carlson et al. ................ 600/544 |
| 2007/0265543 A1 * | 11/2007 | VanSickle et al. ............. 600/544 |
| 2008/0249430 A1 | 10/2008 | John et al. |

* cited by examiner

ELECTRONIC IDENTITY CARD

FIELD OF THE INVENTION

The present invention relates to a systems for evaluating and treating pathologies of the brain and more particularly relates to a device storing data corresponding to a reference baseline of brain electrical activity for use in analyzing electrical activity of the brain to evaluate and/or treat pathologies.

BACKGROUND INFORMATION

Evaluations of physical, physiological and mental disorders are often made through the study of brain electrical activity recorded by an array of electrodes placed on the head or scalp. The resulting data, referred to as an electroencephalograph ("EEG"), measures brain wave activity across a range of frequencies. The advent of quantitative computer analysis has significantly enhanced the clinical utility of the EEG. Neurometric methods of EEG analysis have yielded the quantitative electroencephalogram ("qEEG"), employing mathematical functions to describe healthy and unhealthy brain development and activity. The qEEG provides extensive detail into the electrical activity of the brain not discernible or quantifiable through standard EEG analysis.

SUMMARY OF THE INVENTION

The present invention is directed to a system and method for the acquisition of at least one of qEEG, Brainstem Audio Evoked Response ("BAER") and Event-Related Potential ("ERP") data and storing this data on a storage device such as a card or chip. Furthermore, the present invention is directed to the employment of mobile or immobile devices retrieving the data for the acquisition of subsequent qEEG, BAER and/or ERP measurements. The docking stations may be employed with the functionality to compare initial and subsequent measurements for evaluation purposes.

The present invention is further directed to a method comprising the steps of obtaining a baseline measurement corresponding to a representation of brain activity from a living body and storing the baseline measurements on a storage device configured to be wearable on the living body in combination with obtaining, at a time subsequent to the baseline measurement, a second measurement representing brain activity from the living body, reading the baseline measurement from the storage device and evaluating the living body based on a comparison of the second measurement to the baseline measurement.

The present invention is also directed to a system for analyzing electrical brain activity comprising a component for reading, from a storage medium, data corresponding to a baseline measurement of brain activity of a living body and a component for determining data representing a current brain activity of the living body in combination with a component for evaluating the living body by comparing the baseline measurement data and the current brain activity data.

DETAILED DESCRIPTION

The present invention may be further understood with reference to the following description and the appended drawings. An exemplary embodiment of the present invention is directed to a system and method for the acquisition of a baseline or reference sample of qEEG, a Brainstem Auditory Evoked Response ("BAER") and/or an Event-Related Potential ("ERP") and storing of the aforementioned measurements on a portable electronic medium such as on an identity card or chip or on a mobile device.

The qEEG, BAER and/or ERP may be used for both anticipated evaluations (e.g., monitoring the state of the brain during the course of a chronic condition such as Multiple Sclerosis, Alzheimer's Disease, etc.) or for unanticipated evaluations (i.e, after impact trauma, cerebrovascular accidents such as strokes, etc., Acoustic Neuromas, Central Pontine Myelinolysis, etc.). A system and method is described for taking subsequent measurements of the aforementioned data variables and comparing these measurements to the baseline measurements for evaluation. As described below, a system according to the present invention may reflect or be sensitive to pathologies including, but not limited to, blunt force trauma, multiple sclerosis, cerebrovascular accidents (i.e., strokes, etc.), Acoustic Neuromas and Central Pontine Myelinolysis. In addition, the system may be used to detect transitory impairment due, for example, to drug or alcohol use. If desired, the system may be coupled to a device enabling operation of a vehicle or other machine only after an acceptable reading has been obtained frin the driver. In addition, the system may be used to determine whether a prescribed drug regimen has been followed and/or whether the prescribed regimen is having the intended effect (e.g., whether a dose of anti-depressant was adequate to correct a chronic psychiatric disorder) or whether changes taking place are early warning signs of an incipient problem (e.g., the return of symptoms of central lupus, etc.). When a change of state is found to be persistent (e.g., due to a permanent brain injury or because a suboptimal brain state has been corrected by chronic medication for a psychiatric illness such as ADHD), the baseline data may be updated by this more recent data or a trend across a series of observations can be computed.

Conventional methods for the acquisition of qEEG, BAER and ERP data are known in the art. qEEG data obtained via conventional neurometric analyses typically comprises large files containing a host of data relating to brain electrical activity. In accordance with the exemplary embodiment of the present invention, the qEEG data and/or BAER data and/or ERP data may be compressed to allow an optimization of both the size of the electronic qEEG data file and the amount of relative stored data.

Figure 1:
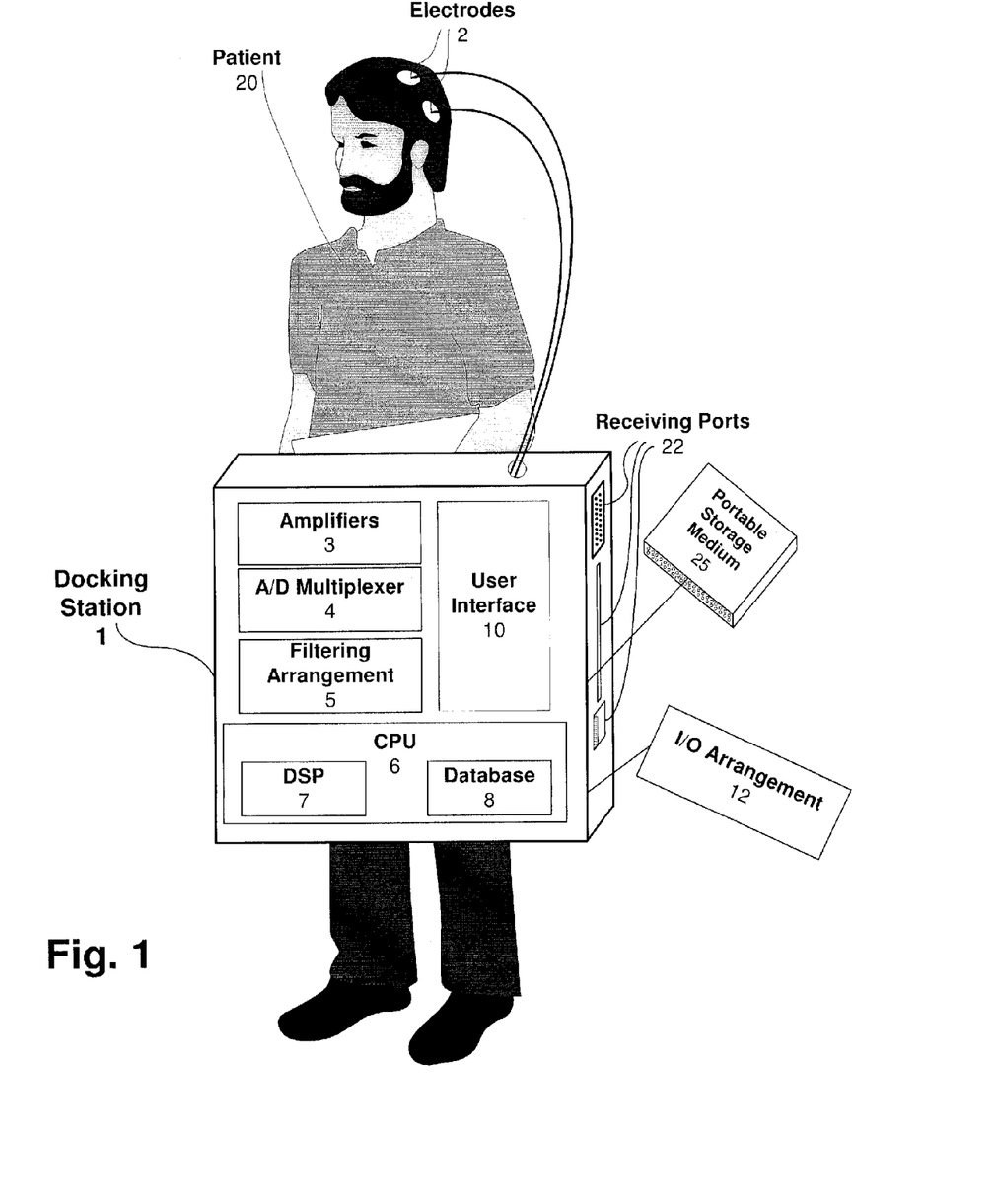
FIG. 1 shows an exemplary embodiment of a system for recording and storing baseline and subsequent neurological data of a patient.

As shown in FIG. 1, an exemplary system according to the present invention includes a computing apparatus receiving data from a series of electrodes 2 placed in contact with the scalp of a patient 20 according to any of a number of methods, as will be described subsequently. The electrodes 2 are connected to a docking station 1, which may be portable or substantially stationary. In an exemplary embodiment of the present invention, the docking station 1 used to perform the baseline qEEG, BAER and/or ERP measurements may be an immobile docking station while a mobile unit is preferable under certain conditions for subsequent measurements. However, those skilled in the art will understand that a portable device may be used for any of the required measurements.

The baseline data may be used as a self-norm for a patient, representing normal brain activity data for the patient with statistical allowances being made to accommodate normal variations, as those skilled in the art would understand.

The analog EEG, BAER and/or ERP signals are digitized via an A/D multiplexer 4, as those skilled in the art will understand to generate digital qEEG, BAER and/or ERP data. As would be understood, the signals may be amplified and/or filtered to remove noise, artifacts and any other unwanted components via a series of amplifiers 3 and filtered to remove noise artifacts using a filtering arrangement 5.

The amplifiers 3, A/D multiplexer 4 and filtering arrangement 5 may be connected to a central processing unit ("CPU") 6 including a dedicated digital signal processor ("DSP") 7 and a database 8. The CPU 6 has an input/output arrangement 12 such as a keyboard, numeric keypad, touch pad or mouse. Once the digital qEEG, BAER and/or ERP data has been recorded, the docking station 1 stores the signals in a database 8 which, in this embodiment is internal to the docking station 1. However, those skilled in the art will understand that this data may be stored on any device connectable to the docking station 1, e.g., via a wired or wireless network. The docking station 1, or any other device connected to the database 8 then writes a selected portion of the data stored in the database 8 (e.g., data corresponding to a particular patient) to a portable storage medium 25 such as a flashcard, chip, disk, card, USB drive, etc. The storage medium 25 may be configured to be wearable on the body by, for example, being mounted on a chain or tether, or by inclusion in a case or other container including a clip or clasp which may be connectable to a piece of clothing. Alternatively, the selected portion of the data may be directly written to the portable storage medium either before or simultaneously with the writing of the data to the database 8. The docking station 1 preferably has the capability to write the selected portion of the data to various portable storage mediums via employment of multiple receiving ports 22 located on the docking station 1. Those skilled in the art will understand that updated baseline measurements may be recorded at time, e.g., annual physician's visits, etc., to constantly refine the operation of the system as will be discussed in greater detail hereinafter. Those skilled in the art will understand that any of the wired electrical connections discussed in this application may be replaced by wireless transmissions to nearby and/or remote components of the systems. For example, electrodes attached to the scalp may use wireless telemetry to communicate with the computing apparatus and any of the individual components of the computing apparatus may communicate with one another through any combination of wired and wireless connections.

Figure 2:
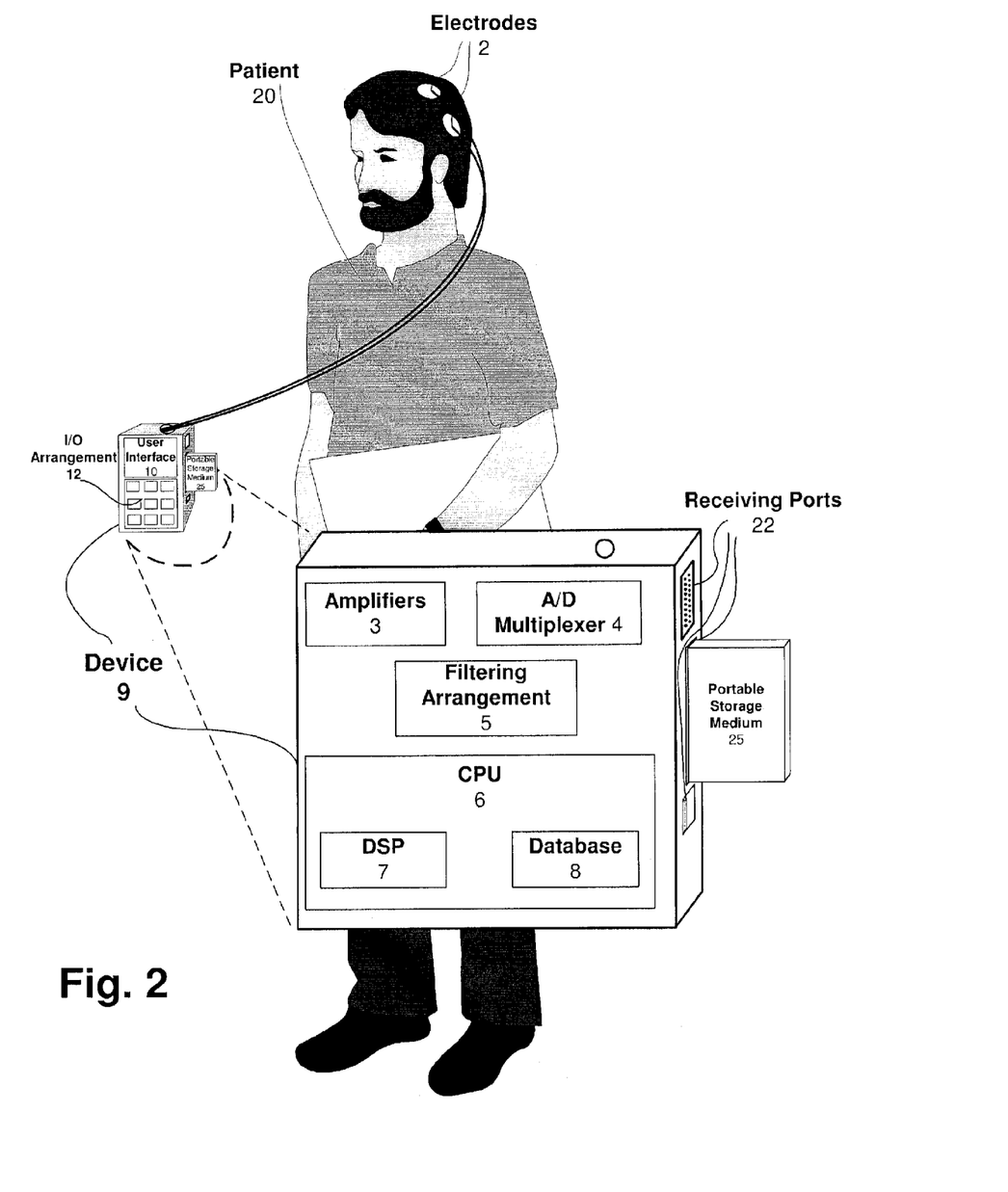
FIG. 2 shows an exemplary embodiment of a system for recording and storing subsequent neurological data of a patient.

As shown in FIG. 2, a device 9 for taking subsequent qEEG, BAER and/or ERP measurements against which the baseline measurements are to be compared for evaluation is formed as a hand-held or otherwise portable device. Those skilled in the art will understand that subsequent measurements may be taken at regular intervals or at any desired number of times in the future with the various differences being analyzed to determine a trajectory or in any other desired manner to enhance the evaluation of brain function and that the description of an initial data reading and a single subsequent reading is illustrative only of a single option. Alternatively, the device 9 may be a portable device equipped and used in manner similar to that described for the docking station 1. To perform a subsequent measurement (e.g., at a subsequent checkup, or after an actual or potential neurological trauma, etc.), a user of the connects the electrodes 2 to the scalp or uses a telemetered array of electrodes as desired and reads current qEEG, BAER and/or ERP data from the patient. The user then inputs data from the storage medium 25 into a receiving port 22 of the device 9. The device 9 may then display on the user interface 10 of the device 9 the baseline qEEG, BAER and/or ERP data and may optionally also display the conditions under which the baseline measurements were recorded (e.g., noise levels, light levels, time of day, etc.) to enable the user to conform to these initial conditions to the extent possible so as to minimize changes in the qEEG, BAER and/or ERP data unrelated to the pathology or change in state.

Figure 3:
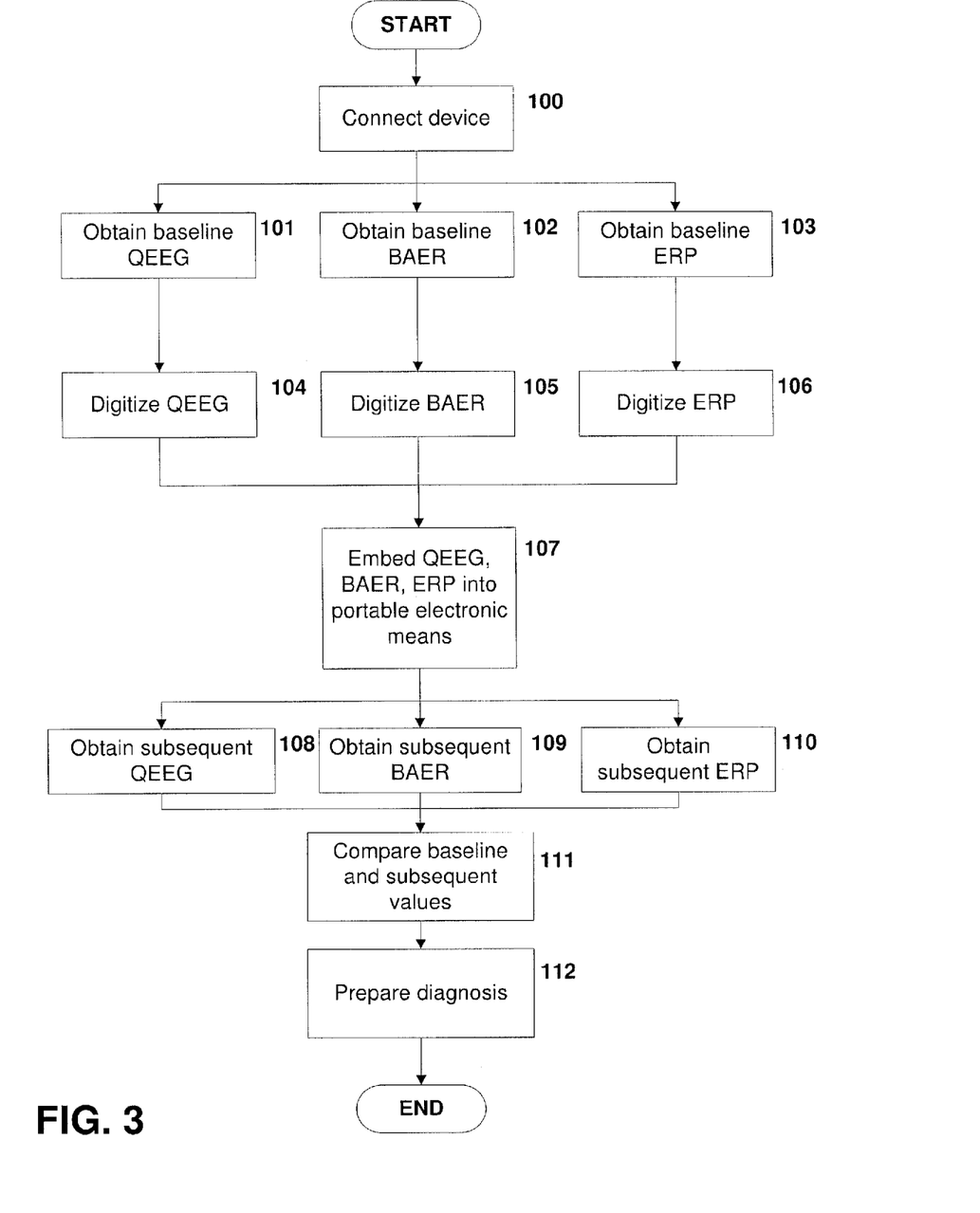
FIG. 3 shows a flow diagram illustrating the operation of the system of the present invention.

An exemplary method illustrating the operation of the system of the present invention is detailed in FIG. 3. In order to record the baseline measurements, a system of electrodes 2 and amplifiers 3, A/D multiplexer 4 and filters 5 of the docking station 1 are connected to a patient 20 (step 100). The electrode placement may be done via any of a number of known positions. For example, a forehead montage may be used, with active electrodes placed on lower and higher portions of the forehead, respectively, and reference electrodes placed on the mastoid (TP10 in the International 10-20 System) or earlobe of the ear contralateral to stimulation, as those skilled in the art will understand. In this preferred embodiment, the electrodes 2 are linked to a data acquisition, analysis, and digital storage docking station 1. Alternatively, the electrode placement may be done via the International 10-20 system, with electrodes 2 placed at least one of nineteen different predefined sites, or any other EEG placement system. The electrodes 2 may be affixed to the scalp of the patient 20 via known methods (i.e., adhesive gels, etc.), using a conductive gel at the attachment points to reduce impedance and prevent electrode noise, as would be understood by those skilled in the art. Alternatively, the electrodes 2 may be affixed to an electrode cap, which may be operably fitted to the scalp of the patient 20 and may provide attachment points for the electrodes 2. As described below, this arrangement is preferable for the acquisition of subsequent data (i.e., at the time of evaluation) in applications directed to sudden neurological trauma in the field (e.g., on a battle or sports field). Electrical activity in various frequency ranges (e.g., wide band ranges or narrow band ranges) or wavelet domains or other selected descriptors from various brain locations for comparison with the data stored for the patient. Differences in electrical potential between the various electrodes 2 are analyzed by the docking station 1 may detect and record the electrical activity of the brain by detecting differences in electrical potential between electrodes 2 placed at the various sites (step 101).

The first set of measurements recorded from a patient 20 are designated as a baseline measurement for that individual. (Steps 101-103) Accuracy of the qEEG data is especially important when performing the baseline measurements, as they will be used for comparison against future measurements to make evaluations. Thus, the baseline measurements are preferably performed under controlled settings to minimize the impact on the qEEG data by factors other than the pathology (e.g., varying levels of noise, light, etc.). Those skilled in the art will understand that, even in a controlled environment, the brain's electrical activity will fluctuate to some degree. Therefore, measurements taken to establish the baseline reading are preferably repeated to obtain a more accurate assessment of their variance and/or standard deviation. Those skilled in the art will understand that the variance and/or standard deviation may be referred to in future analyses to establish a range of normal values for the patient 20, thereby minimizing the potential for misdiagnosis.

To minimize the amount of data required on the portable storage medium 25, the qEEG signals are digitized, for example, into a set of about 2000 standard scores (step 102) with each of the scores represented by a two digit number relating to qEEG values or ERP values at pre-set time intervals. The qEEG may be further resealed using known means (i.e., spectral analysis, digital filtering, etc.) to reduce the file size and eliminate detail and noise irrelevant to or whose relevance is insignificant to future evaluations. As those skilled in the art will understand, filtering the QEEG signal minimizes the impact of extraneous noise as well as artifacts (e.g., signals corresponding to movement of the eyes, cardiac activity, electromyogram artifacts, glossokinetic artifacts, etc.).

The qEEG is typically used to monitor particular conditions, some of which are noted above. Based on the symptoms exhibited by a patient 20, an evaluator may choose to perform subsequent measurements to affirm or rule out other possible conditions, as are discussed more fully below. Accordingly, when performing baseline measurements, an evaluator may also record the patient's 20 BAER and ERP.

In step 103, a baseline BAER measurement is established. As understood by those skilled in the art, BAER measures the rate of transmission of auditory information along the eighth cranial nerve, also referred to as the auditory nerve, from the ear to the brainstem. Specifically, BAER determines the times at which neural signals time locked to auditory stimuli are transmitted through various anatomical structures to determine the rate of transmission along various parts of this neural pathway. The points in time at which each signal passes through the various anatomical structures are determined by locating a series voltage peaks. As this rate of transmission can be slowed by lesions in the pons area of the brainstem, from which the eighth cranial nerve arises, and other abnormalities, BAER data showing a latency or delay in any of the various peaks is indicative of the presence of one or more such abnormalities along the pathway. The BAER baseline data record "normal" nerve transmission speeds for a patient, for comparison with values at a later date or after a trauma to evaluate lesions and/or other brain pathologies.

BAER data is elicited by supplying repeated auditory clicks to one ear while the other ear receives a masking noise of a lesser intensity. A BAER testing procedure comprises a series of clicks presented at desired intervals, intensities and pulse widths. For example, an exemplary procedure may comprise two to three thousand auditory clicks at about a 80-90 decibel Sensorineural Hearing Level ("SHL") with each click having a pulse width of, for example, 100 μs presented at a 0.1 ms interval across the latency epoch from 0 to 12.8 ms. Those skilled in the art will understand the importance of the repetition of the elicited stimulus to average out and thereby cancel background noise.

The BAER data may be filtered by any form of signal analysis, as those skilled in the art will understand to remove unwanted portions of the raw data and then compressed and represented as a series of, for example, 128 numbers, each representing an timing of the various signal peaks representing transmission of the signal through various structures.

The BAER data is affected by a range of factors including age, sex, auditory acuity, stimulus repetition rate, intensity and polarity. It is therefore preferred that, when the baseline BAER measurement is taken and recorded, present values of at least a selected set of the aforementioned factors be recorded as well. When subsequent measurements are taken, the initial value of these factors may be referred to and accounted for in making the evaluation. If current values are available, these may used as well. For instance, an evaluator performing a subsequent BAER measurement may adhere to a stimulus repetition rate, intensity and polarity values the same as those employed in establishing the baseline BAER data to minimize discrepancies. Furthermore, an evaluator and or the device 9 performing the evaluation, as will be explained later, may take into account the age and the time elapsed since the establishment of the baseline BAER data when analyzing the latencies of the various peaks of the current BAER data, as those skilled in the art will understand.

The baseline measurements may further include extracted cognitive Event Related Potential ("ERP") data, also referred to as a P300 data (step 104). The ERP data is indicative of the brain's responses to unpredictable stimuli. Accordingly, an ERP testing procedure comprises the provision to a patient 20 of both common and rare visual, auditory, tactile, gustatory or olfactory stimuli. Those skilled in the art will understand that the employment of both common and rare stimuli may enhance the accuracy with which a patient's response to stimuli may be gauged. For example, the brain responds differently to stimuli to which it is exposed constantly than it does to rarely encountered or unexpected stimuli.

In an exemplary embodiment, a series of common tones of a first frequency (e.g., 1,000 Hz) may be provided in conjunction with rare or unexpected tones of a second frequency (e.g., 3,000 Hz). Each of the tones elicits different brain electrical activity which may be detected via electrophysiological amplifiers with well-known specifications and recorded in a number of well known standardized sets, as those skilled in the art will understand. As described above, either of the common and rare or unexpected stimuli may be applied in a variety of modalities and it is important that, for subsequent measurements, the type and intensity of these stimuli be matched as closely as possible to the stimuli used to establish the baseline ERP data. To that end, values representing these variables are preferably stored along with the baseline ERP data to facilitate their reproduction and/or to account for any differences in these values in subsequent measurements. As described in respect to the BAER testing procedure, baseline ERP measurements are preferably repeated a several times to enhance the accuracy of the values obtained by reducing the impact of noise. The ERP data may be filtered by any form of signal analysis to reduce noise and artifact related components of the data, as those skilled in the art will understand.

The ERP data are preferably represented as a series of about 100 numbers, each representing an ERP voltage level at 5 ms intervals across a latency epoch of 0 to 500 ms (step 106). Because ERP results typically appear in the vicinity of 300 ms, those skilled in the art will understand that a latency epoch of 0 to 500 ms is preferred to minimize situations where a peak falls outside the latency epoch while also minimizing the retention of extraneous data and reducing the amount of data which needs to be stored on the portable storage medium 25. The aforementioned qEEG, BAER and/or ERP measurements are then stored on a portable electronic medium 25 as baseline reference values (step 107) for the patient 20.

The device 9 performing the subsequent analysis may require a user to input data corresponding to current environmental conditions and automatically account for any differences between these current environmental conditions and baseline environmental conditions stored for the baseline data. The baseline date for the environmental conditions may include at least one of a light intensity, a sound level, an environmental temperature, and a body temperature. As yet another alternative, the device 9 may be equipped with the capability to automatically measure and record data corresponding to such environmental conditions eliminating the need for a user to manually input these values. Those skilled in the art will understand that the measurement of the aforementioned variables may be done via techniques known in the art such as the use of digital sound level meters, photodetectors, etc. coupled to a processing unit of the device 9.

A set of numerical descriptors are extracted to quantify the qEEG, BAER and/or ERP as well as their mean values, variance, standard deviation and environmental conditions for storage in either or both of the database 8 and/or on the portable storage medium 25. Those skilled in the art will understand that the portable retention of the qEEG, BAER and/or ERP data may be in various alternate manners, such as, but not limited to solid state memory devices such as USB flash drives, memory sticks, zip drives, and CD-ROMs.

The qEEG, BAER and/or ERP data collectively provide a compact but comprehensive insight into brain function. By quantifying the aforementioned baseline measurements and storing them on the portable storage medium 25, the exemplary embodiment of the present invention provides to an evaluator a readily accessible history of brain function of a patient 20 enabling rapid and accurate evaluation of a wide range of pathologies of the brain.

After storage of the baseline measurements on the portable electronic means 25 as discussed earlier, the measurements can be referenced at any time when taking subsequent measurements. For example, the portable storage medium 25 may be carried by the patient 20 at all times (e.g., as a dog tag, in a wallet, on a medical bracelet, etc.). The ready availability of the portable electronic means 25 and the reduced amount of data required to provide this overview of brain function allows the device 9 to make a rapid and accurate evaluation under a wide range of conditions even far from medical facilities (e.g., on a battle field, in a sports arena, etc.). Alternatively, such subsequent measurements may be made at a clinic (e.g., at annual physicians visits, etc.).

In step 108, the subsequent qEEG, BAER and/or ERP data measurements are taken (steps 109, 110). The quick electrode placement allowed by the arrangement of electrodes at preselected locations in a cap may be employed with the portable device 9 to speed the evaluation by eliminating the time required to apply individual electrodes. The portable storage medium 25 is retrieved from the patient 20 and plugged into the receiving port 22 of the device 9 (step 111). The device 9 then accesses the patient data stored in the database 8 and compares it to the data on the portable storage medium 25 as described in more detail below. As would be understood by those skilled in the art, for applications utilizing BAER or ERP data, the device 9 will include or be used in conjunction with apparatus for applying the desired pattern of sensory stimuli to the patient 20 (e.g., headphones supplying tone pips) in the desired pattern. The device 9 may display the analysis of the data in a number of manners. For example, the device 9 may identify one or more topographical areas of the brain evidencing a significant change in activity, specifying the nature of the change (i.e., slowed or increased reaction to a stimulus, lack of activity, etc.). When making the comparison between the two sets of measurements, the portable device 9 preferably takes into account the variances and standard deviation of the baseline measurements to provide an evaluator as would be understood. The device 9 and/or the evaluator may then make an evaluation based on the detected changes in the qEEG, BAER and/or ERP (step 112).

The device 9 of the exemplary embodiment may possess the functionality to automatically detect differences between the baseline data and subsequent qEEG, BAER and/or ERP data. This may be done by quantifying the latency and amplitudes of the peaks of the subsequent qEEG, BAER and/or ERP data and identifying specific differences between these values and the values stored in the portable storage medium 25. The device 9 in one embodiment, is programmed to compare these differences to one or more standard deviation values generated during the recording of the baseline data and, to correlate differences of specific values with specific pathologies as would be understood by those skilled in the art. For example, an increase in generalized 3 Hz spike and wave discharges may be interpreted by the device 9 as indicative of childhood epilepsy.

In addition, the device 9 and/or the docking station 1 may be equipped to receive data from an operator or to detect through repeated subsequent measurements that changes have occurred that are likely to have caused permanent and persistent or clinically significant changes in electrical brain activity (e.g., stroke or other non-correctable brain damage, concussion, traumatic brain injury, or correction of a suboptimal brain state, etc.), and to replace earlier baseline data with new qEEG, BAER and/or ERP baseline values more accurately reflecting this new persistent state.

Because of the widely encompassing evaluation utility of brain electrical activity and, in particular, the qEEG, the BAER and the ERP, the applications of the exemplary embodiments of the present invention are vast. Though only a limited number of applications are noted herein, it is noted that the exemplary embodiment of the present invention may be applied in a host of alternate manners without deviating from the scope of the present invention.

For example, the portable storage medium 25 according to the present invention may be carried by any individual, regardless of medical history or probability of risk of trauma. In the event of any potential traumatizing incident such as a car accident, the stored data may be referred to by an evaluator to determine the scope and/or type of brain injury. For example, if an individual is exhibiting symptoms indicative of a neurosystematic injury, an evaluator may perform quick qEEG, BAER and/or ERP measurements using the portable device 9 and generate a preliminary evaluation on the spot allowing emergency treatment to be focused toward this evaluation and away from treatments that might exacerbate the situation.

The portable storage medium 25 is preferably worn on or carried by an individual in a location readily accessible to an evaluator. For example, the portable storage medium 25 may be secured to a chain or cord and worn around the arm or neck similar to or in replacement of an army dogtag. It is common procedure for emergency medical respondents to check for medical bracelets when responding to a medical emergencies. By wearing the card and/or chip of the present invention on one's aim or neck, a respondent may be alerted to the possibility of administering diagnostic qEEG, BAER and/or ERP even where the patient 20 is unable to communicate this information due to the medical condition. Furthermore, as would be understood by those skilled in the art, depending on the capacity of the portable storage medium 25, any or all of a wide variety of additional types of information may be stored including patient identification data, emergency contact data, a listing of allergies, brain scan data selected to enable the device 9 to positively establish whether the person carrying the portable storage medium 25 is the source of the baseline data, relevant DNA sequence information, etc.

Furthermore, in situations where it is desirable to ensure that an individual is unimpaired (e.g., individuals operating heavy machinery, pilots, drivers of mass transit vehicles, etc.), a portable storage medium 25 may include baseline data enabling detection of any relevant mental impairment (e.g., due to alcohol, drug use, medical condition, lack of sleep, etc.). Upon the commencement of a shift, the individual couples electrodes to his scalp (e.g., by donning an elastic cap including built in electrodes) and plugs his portable storage medium 25 into the device 9 which compares the current data to the baseline data to detect and/or measure any impairment. As would be understood by those skilled in the art, the device 9 may be designed so that when an impairment is detected, an alarm of the condition is provided to the individual and/or to a supervisor, etc. Alternatively, the device 9 may be coupled to the equipment the individual is to operate preventing the individual from operating the equipment while the impairment exists. This functionality is preferably coupled with the brain scan identification functionality described above to ensure that the person providing the current data is the desired operator of the equipment.

Employment of the exemplary embodiment of the present invention may be particularly useful to those suffering from medical conditions that currently interfere with day to day life preventing them from holding positions, performing actions and/or participating in activities from which they are currently restricted. For example, individuals suffering from epilepsy may be unable to drive or perform other tasks due to the risk of seizure. With the current system, such individuals may perform routine (i.e., daily, weekly, etc.) measurements to check for brain electrical activity indicative of an oncoming epileptiform event so that the individual may take advantage of times when the current brain activity indicates that the current risk of such an event is low (e.g., below a selected threshold) to partake of the activity. A range of risk levels or other objective criteria corresponding to the particular condition and the associated brain activity may be established where such permission may have legal consequences (e.g., driving restrictions, etc.). For example, sufferers of epilepsy may reduce the risk of accident by taking appropriate precautions when risk of an epileptiform event is high or when such an event is indicated as imminent.

Furthermore, the exemplary embodiment of the present invention may be used to detect warning signs of brain damaging events such as stroke. In the case of stroke, such warning signs may include transient ischemic attacks, etc. in patients with a personal or family history of heart disease, diabetes, etc.

Furthermore, regular monitoring of the qEEG, BAER and/or ERP in accordance with the present invention allows regular monitoring of a variety of non-pathological conditions including, but not limited to, determining whether an administered dosage of psychoactive medicine (e.g., anti-depressants or stimulants provided to children diagnosed with ADHD) or across multiple sessions to establish a dose response curve for optimization of dosage. In addition, the system may be employed to detect warning signs of incipient problems (e.g., the return of symptoms of central lupus, etc.) or utilization of substances of abuse (e.g., marijuana or cocaine abuse in adolescence). Those skilled in the art will understand that the list of potential applications of such brain electrical activity monitoring will change with continued research into medical conditions and their correlation to such brain electrical activity.

Accordingly, the exemplary embodiment of the present invention may be used for sobriety checks such as, for example, in lieu of a breathalyser test. In such a case, the user interface 10 of the portable device used for conducting the sobriety test may be simplified so that the device 9 may self determine abnormal activities without requiring data analysis by the user of the device. Carrying such a device may, for example, be part of a court ordered regimen for convicted drunk drivers, etc.

Furthermore, docking stations may be established to provide ready access to devices for administration of the qEEG, BAER and/or ERP. The docking stations may comprise of amplifiers, stimulators, means of connection of the electrodes and receiving ports for the card and/or chip of the exemplary embodiment of the present invention. The docking stations may possess the capability to administer subsequent measurements and compare the two sets of measurements, taking into account acceptable variations in the data as described earlier. The docking stations may be located in physician's offices, school offices, pharmacies, supermarkets or other shopping complexes, military medical stations, etc. The docking stations may also be portable stations, employing the use of portable handheld devices.

The employment of the docking station may further provide end users the option of having their qEEG, BAER and/or ERP measurements taken more frequently, which may be necessary in the cases of individuals with conditions that require constant monitoring. Performing regular measurements may help an evaluator determine if a dosage of medicine is adequate in treating a condition without harmful side effects. For example, checkups at docking stations may determine if excessive medication prescribed for hypertension led to inadequate cerebral perfusion pressures. Alternatively, regular measurements may be useful to check the progression of an untreatable affliction, such as Parkinson's Disease, Alzheimer's Disease, Bipolar Disorder, Down Syndrome, etc. in a patient.

Additionally, a software program may be developed to allow presently available EEG instruments to be adaptable for use with the card and/or chip of the present invention for qEEG analysis. Such software may be installed on both portable and non-portable devices, as those skilled in the art will understand.

Other embodiments of the invention will be apparent to those skilled in the art from consideration of the specification and practice of the invention disclosed herein. Thus, it is intended that the present invention cover the modifications and variations of this invention provided they come within the scope of the appended claims and their equivalents.

What is claimed is:

1. A method comprising:
    receiving, using electrodes, a baseline measurement corresponding to a representation of brain activity from a living body;
    storing the baseline measurements on a storage device configured to be wearable on the living body;
    obtaining, using electrodes connected to a portable device, at a time subsequent to the baseline measurement, a second measurement representing brain activity from the living body;
    evaluating, via a processing unit of the portable device, the living body based on a comparison of the second measurement to the baseline measurement stored in the storage device, wherein the storage device is portable independently of the portable device;
    determining, via the processing unit of the portable device, whether the second measurement is indicative of a persistent change in the brain activity of the living body;
    replacing, via one of the portable device and a docking station, the baseline measurement with a current measurement if the second measurement is indicative of a persistent change in the brain activity of the living body; and
    determining, via the processing unit, if the living body is experiencing an impairment based on the comparison of the baseline data to the current brain activity data, wherein if an impairment is detected, the processing unit prevents operation of a machine operably associated with the system.

2. The method of claim 1, wherein the brain activity measurement is at least one of a qEEG, a BAER and an ERP.

3. The method of claim 1, further comprising filtering noise from the baseline measurement via a filtering arrangement.

4. The method of claim 1, further comprising amplifying the baseline measurement via an amplifier.

5. The method of claim 1, further comprising storing personal data about the living body on the portable storage device.

6. The method of claim 5, wherein the personal data includes age, sex, date, and time of measurement.

7. The method of claim 1, further comprising obtaining the measurements by using one of a montage including leads on a forehead of the living body and any selected array from the International 10-20 System with any selected reference.

8. The method of claim 1, wherein the baseline measurement is performed at the docking station.

9. The method according to claim 8, wherein the docking station is mobile.

10. The method of claim 8, wherein the baseline measurement is transmitted to a database via one of a wired and a wireless network, the docking station writing the baseline measurement from the database to the storage device.

11. The method according to claim 1, wherein the storage device includes one of a USB drive, a memory card, a memory stick, a memory chip, a CD-ROM, a floppy disk, a zip disk and a flash card.

12. The method according to claim 1, wherein the evaluating includes performing a substance abuse check on the living body based on the comparison.

13. The method according to claim 1, wherein the evaluating includes determining an extent of trauma on the living body.

14. The method according to claim 1, wherein the evaluating includes checking an effectiveness of one of a medical and a neurological treatment on the living body.

15. The method of claim 1, wherein the replacement measurement is obtained at one of a predetermined interval from the baseline measurement and upon occurrence of one of a clinically significant neurological event and a clinically significant medical event.

16. The method of claim 1, wherein the representation of brain activity from the living body corresponds to normal brain activity.

17. The method of claim 1, further comprising:
referencing, by the processing unit of the portable device, at least one baseline environmental condition stored on the storage device; and
conforming, by the processing unit of the portable device, at least one current environmental condition to the at least one baseline environmental condition when performing current data measurements;
wherein the baseline environmental condition is at least one of a light intensity, sound level, environmental temperature and a body temperature.

18. The method of claim 1, wherein the machine is a vehicle.

19. The method of claim 1, wherein if an impairment is detected, the processing unit generates an alarm.

20. A method comprising:
receiving, in a processing unit of a first device, baseline data representing brain activity of a living body from a storage device configured to be wearable on the living body;
obtaining, using electrodes connected to a portable device, current data representing a current brain activity of the living body;
evaluating, via a processing unit of the portable device, the living body by comparing the baseline data stored in the storage device to the current data, wherein the storage device is portable independent of the portable device;
determining, via the processing unit of the portable device, whether the second measurement is indicative of a persistent change in the brain activity of the living body;
replacing, via one of the portable device and a docking station, the baseline data with current data if the second measurement is indicative of a persistent change in the brain activity of the living body; and
determining, via the processing unit, if the living body is experiencing an impairment based on the comparison of the baseline data to the current brain activity data, wherein if an impairment is detected, the processing unit prevents operation of a machine operably associated with the system.

21. The method of claim 20, further comprising:
referencing, by the processing unit of the portable device, at least one baseline environmental condition stored on the storage device; and
conforming, by the processing unit of the portable device, at least one current environmental condition to the at least one baseline environmental condition when performing current data measurements.

22. The method of claim 21, wherein the at least one baseline environmental condition includes at least one of an environmental temperature, a body temperature, a light intensity and a sound level.

23. The method of claim 21, wherein the at least one baseline environmental condition is one of a light intensity and a sound level.

24. The method of claim 20, wherein the machine is a vehicle.

25. The method of claim 20, wherein if an impairment is detected, the processing unit generates an alarm.

26. A system for analyzing electrical brain activity, the system comprising:
a first component configured to read from a portable storage medium, data corresponding to a baseline measurement of brain activity of a living body;
a second component configured to determine data representing a current brain activity of the living body; and
a third component provided on a portable device and configured to evaluate the living body by comparing the baseline measurement data stored in the portable storage medium and the current brain activity data, wherein the portable storage medium is portable independently of the portable device, the third component configured to determine whether the second measurement is indicative of a persistent change in the brain activity of the living body and replace the baseline measurement with a current measurement if the second measurement is indicative of a persistent change in the brain activity of the living body, the third component being further configured to determine if the living body is experiencing an impairment based on the comparison of the baseline data to the current brain activity data, wherein if an impairment is detected, the third component prevents operation of a machine operably associated with the system.

27. The system of claim 26, further comprising a first arrangement configured to amplify, filter and sample one of the baseline measurement and the current brain activity measurement.

28. The system of claim 26, further comprising a second arrangement configured to digitize the baseline measurements.

29. The system of claim 26, further comprising a third arrangement configured to quantify a difference in the baseline measurement and current brain activity data, wherein the third component is configured to assess the living body based on one of the quantified difference and a trajectory corresponding to the difference.

30. The system of claim 29, wherein an evaluation by the third component is provided to a user on a user interface.

31. The system of claim 26, further comprising a fourth arrangement configured to quantify a difference in the baseline measurement and current brain activity data and display one of the difference and a trajectory corresponding to the difference on a user interface.

32. The system of claim 31, wherein the third component is configured to evaluate the living body based on one of the quantified difference and a trajectory corresponding to the difference.

33. The system of claim 26, wherein the machine is a vehicle.

34. The system of claim 26, wherein if an impairment is detected, the third component generates an alarm.

35. The system of claim 26, wherein the portable storage medium further stores a baseline environmental condition, the baseline environmental condition being at least one of a light intensity, sound level, environmental temperature and a body temperature.

36. A method, comprising:
receiving, using electrodes, a baseline measurement corresponding to a representation of brain activity from a living body;
storing the baseline measurements on a storage device configured to be wearable on the living body;
obtaining, using electrodes connected to a portable device, at a time subsequent to the baseline measurement, a second measurement representing brain activity from the living body;
evaluating, via a processing unit of the portable device, the living body based on a comparison of the second measurement to the baseline measurement stored in the storage device, wherein the storage device is portable independently of the portable device;
determining, via the processing unit of the portable device, whether the second measurement is indicative of a persistent change in the brain activity of the living body;
replacing, via one of the portable device and a docking station, the baseline measurement with a current measurement if the second measurement is indicative of a persistent change in the brain activity of the living body;
referencing, by the processing unit of the portable device, at least one baseline environmental condition stored on the storage device;
conforming, by the processing unit of the portable device, at least one current environmental condition to the at least one baseline environmental condition when performing current data measurements, wherein the at least one baseline environmental condition is one of a light intensity and a sound level; and
determining, via the processing unit, if the living body is experiencing an impairment based on the comparison of the baseline data to the current brain activity data, wherein if an impairment is detected, the processing unit prevents operation of a machine operably associated with the system.

37. The method of claim 36, wherein the at least one baseline environmental condition includes at least one of an environmental temperature and a body temperature.

38. The method of claim 36, wherein the machine is a vehicle.

39. The method of claim 36, wherein if an impairment is detected, the processing unit generates an alarm.

40. A method, comprising:
receiving, in a processing unit of a first device, baseline data representing brain activity of a living body from a storage device configured to be wearable on the living body;
obtaining, using electrodes connected to a portable device, current data representing a current brain activity of the living body;
evaluating, via a processing unit of the portable device, the living body by comparing the baseline data stored in the storage device to the current data, wherein the storage device is portable independent of the portable device;
determining, via the processing unit of the portable device, whether the second measurement is indicative of a persistent change in the brain activity of the living body;
replacing, via one of the portable device and a docking station, the baseline data with current data if the second measurement is indicative of a persistent change in the brain activity of the living body;
referencing, by the processing unit of the portable device, at least one baseline environmental condition stored on the storage device;
conforming, by the processing unit of the portable device, at least one current environmental condition to the at least one baseline environmental condition when performing current data measurements, wherein the at least one baseline environmental condition is one of a light intensity and a sound level; and
determining, via the processing unit, if the living body is experiencing an impairment based on the comparison of the baseline data to the current brain activity data, wherein if an impairment is detected, the processing unit prevents operation of a machine operably associated with the system.

41. The method of claim 40, wherein the at least one baseline environmental condition includes at least one of an environmental temperature and a body temperature.

42. The method of claim 40, wherein the machine is a vehicle.

43. The method of claim 40, wherein if an impairment is detected, the processing unit generates an alarm.

44. A system for analyzing electrical brain activity, comprising:
a first component configured to read from a portable storage medium, data corresponding to a baseline measurement of brain activity of a living body;
a second component configured to determine data representing a current brain activity of the living body; and
a third component provided on a portable device and configured to evaluate the living body by comparing the baseline measurement data stored in the portable storage medium and the current brain activity data, wherein the portable storage medium is portable independently of the portable device, the third component configured to determine whether the second measurement is indicative of a persistent change in the brain activity of the living body and replace the baseline measurement with a current measurement if the second measurement is indicative of a persistent change in the brain activity of the living body, the third component being configured to reference at least one baseline environmental condition stored on the storage device and conform at least one current environmental condition to the at least one baseline environmental condition when performing current data measurements, wherein the at least one baseline environmental condition is one of a light intensity and a sound level, and wherein the third component is further configured to determine if the living body is experiencing an impairment based on the comparison of the baseline data to the current brain activity data, wherein if an impairment is detected, the third component prevents operation of a machine operably associated with the system.

45. The system of claim 44, wherein the at least one baseline environmental condition includes at least one of an environmental temperature and a body temperature.

46. The method of claim 44, wherein the machine is a vehicle.

47. The method of claim 44, wherein if an impairment is detected, the third component generates an alarm.

\* \* \* \* \*